(12) United States Patent  
Amagai et al.

(10) Patent No.: US 7,060,868 B1  
(45) Date of Patent: Jun. 13, 2006

(54) AUTOIMMUNE DISEASE MODEL ANIMAL

(75) Inventors: Masayuki Amagai, Tokyo (JP); Takeji Nishikawa, Tokyo (JP); Harumi Suzuki, Tokyo (JP); Shigeo Koyasu, Tokyo (JP)

(73) Assignee: Keio University, Tokyo (JP)

( * ) Notice: Subject to any disclaimer, the term of this patent is extended or adjusted under 35 U.S.C. 154(b) by 0 days.

(21) Appl. No.: 09/937,739

(22) PCT Filed: Mar. 30, 2000

(86) PCT No.: PCT/JP00/02023

§ 371 (c)(1),  
(2), (4) Date: Mar. 14, 2002

(87) PCT Pub. No.: WO00/57695

PCT Pub. Date: Oct. 5, 2000

(30) Foreign Application Priority Data

Mar. 31, 1999 (JP) .................................. 11/091408

(51) Int. Cl.  
*A01K 67/00* (2006.01)  
*A61K 39/00* (2006.01)  
*A61K 48/00* (2006.01)  
*A01N 65/00* (2006.01)

(52) U.S. Cl. ................ 800/9; 800/8; 800/13; 424/93.1; 424/93.21; 424/184.1

(58) Field of Classification Search ................ 800/8–13  
See application file for complete search history.

(56) References Cited

OTHER PUBLICATIONS

Logan and Sharma, Clin Exp Pharmacol Physiol Dec. 1999; 26:1020-25.*  
Linder, Lab Animal May 2001;30:34-9.*  
Mullins et al, J Clin Invest Apr. 1996;97:1557-60.*  
Yamamura, Prog Exp Tumor Res Basel, Karger, 1999;35:13-24.*  
Janeways Jr., Immunobiology, 5th Edition, c2001.*  
Braley-Mullen et al, J Immunol 1994;152:307-14.*  
Schloot et al, J Autoimmun 1996;9:357-63.*  
Yanagimachi, Mol Cell Endocrinol 2002;187:241-8.*  
Denning, Nat Biotech 2001;19:559-562.*  
Humpherys et al, Science 2001;293:95-97.*  
Pearson, Nature 2002;415:8-9.*  
Kaufman et al, J Clin Invest 1992;89:283-292.*  
Clemente et al, J Clin Endocrin & Metabol 1997;82:1353-61.*  
Xiao et al, J Clin Invest Oct. 2002;110:955-63.*  
Aratani et al, Infect Immunity Apr. 1999;67:1828-36.*  
Amagai et al., "Use of Autoantigen-Knockout Mice in Developing an Active Autoimmune Disease Model for Pemphigus," *J. Clin. Invest.*, 105(5):625-631 (2000).

Fan et al., "BALB/c Mice Produce Blister-Causing Antibodies Upon Immunization with a Recombinant Human Desmoglein 3[1]," *J. Immunol.*, 163:6228-6235 (1999).  
Ono et al., *Igaku no Ayumi*, pp. 282-284 (1995) (abstract).  
Amagai et al., "Desmoglein 3 (Pemphigus vulgaris Antigen) as a Major Autoimmune Target in Paraneoplastic Pemphigus and Its Role in Pathogenesis," *J. Invest. Dermatol.*, 110:482 (1998) (abstract).  
Koch et al., "Targeted Disruption of the Pemphigus Vulgaris Antigen (Desmoglein 3) Gene in Mice Causes Loss of Keratinocyte Cell Adhesion with a Phenotype Similar to Pemphigus Vulgaris," *J. Cell Biology*, 137(5):1091-1102 (1997).  
Juhasz et al., "Development of Pemphigus Vulgaris-Like Lesions in Severe Combined Immunodeficiency Disease Mice Reconstituted with Lymphocytes from Patients," *J. Clin. Invest*, 92:2401-2407 (1993).  
Stanley, "Cell Adhesion Molecules as Targets of Autoantibodies in Pemphigus and Pemphigoid, Bullous Diseases Due to Defective Epidermal Cell Adhesion," *Adv. Immunol.*, 53:291-325 (1993).  
Goodnow, "Balancing Immunity and Tolerance: Deleting and Tuning Lymphocyte Repertoires," *Proc. Natl. Acad. Sci. USA*, 93:2264-2271 (1996).  
MacDonald, "Mechanisms of Immunological Tolerance," *Science*, 246:982 (1989).  
Bach et al., "Are There Unique Autoantigens Triggering Autoimmune Diseases?" *Immunol. Rev.*, 164:139-155 (1998).  
Hashimoto et al., "Anti-Cell Surface Pemphigus Autoantibody Stimulates Plasminogen Activator Activity of Human Epidermal Cells," *J. Exp. Med.*, 157:259-272 (1983).  
Anhalt et al., "Induction of Pemphigus in Neonatal Mice by Passive Transfer of IgG From Patients with the Disease," *N. Engl. J. Med.*, 306:1189-1196 (1982).

(Continued)

*Primary Examiner*—Q. Janice Li  
(74) *Attorney, Agent, or Firm*—Nixon Peabody LLP

(57) ABSTRACT

*Pemphigus vulgaris* (PV) is an autoimmune disease with a possible fatality of the skin and mucosae which is induced by an antibody against desmoglein 3 (Dsg3). Persistent production of anti-Dsg3 IgG can be induced by adoptively transferring spleen cells of a DSG3–/– mouse immunized with rDsg3 into an RAG2–/– immunodeficient mouse expressing Dsg3 protein. This IgG in the blood binds to the Dsg3 protein in vivo, induces the breakage of intercellular adhesion of keratinocytes and thus brings about the phenotype of *pemphigus vulgaris* involving the formation of blisters in the oral mucosa and the disappearance of resting hair. These effects are sustained over 6 months. By using this method, active disease model animals relating to various autoimmune diseases can be constructed.

4 Claims, 4 Drawing Sheets

OTHER PUBLICATIONS

Schultz et al., "Development of CD4⁻CD8⁻αβTCR⁺NKI.1⁺T Lymphocytes," *J. Immunol.*, 157:4379-4389 (1996).

Koch et al., "Desmoglein 3 Anchors Telogen Hair in the Follicle," *J. Cell Sci.*, 111:2529-2537 (1998).

Schlitz et al., "Production of Epidermal Acantholysis in Normal Human Skin In Vitro by the IgG Fraction From Pemphigus Serum," *J. Invest. Dermatol.*, 67:254-260 (1976).

Ishii et al., "Charcterization of Autoantibodies in Pemphigus Using Antigen-Specific Enzyme-Linked Immunosorbent Assays With Baculovirus-Expressed Recombinant Desmogleins," *J. Immunol.*, 159:2010-2017 (1997).

Amagai et al., "Antigen-Specific Immunoadsorption of Pathogenic Autoantibodies in Pemphigus Foliaceus," *J. Invest. Dermatol.*, 104:895-901 (1995).

Amagai, "Pemphigus: Autoimmunity to Epidermal Cell Adhesion Molecules," *Adv. Dermatol.*, 11:319-352 (1996).

Amagai et al., "Autoantibodies Against a Novel Epithelial Cadherin in Pemphigus Vulgaris, a Disease of Cell Adhesion," *Cell*, 67:869-877 (1991).

Amagai et al., "Antibodies Against Desmoglein 3 (Pemphigus Vulgaris Antigen) Are Present in Sera from Patients With Paraneoplastic Pemphigus and Cause Acantholysis In Vivo in Neonatal Mice," *J. Clin. Invest.*, 102:775-782 (1998).

Amagai et al., "Usefulness of Enzyme-Linked Immunosorbent Assay Using Recombinant Desmogleins 1 and 3 for Serodiagnosis of Pemphigus," *Br. J. Dermatol.*, 140:351-357 (1999).

Dry, "The Coat of the Mouse (*Mus musculus*)," in Bateson, eds., *Journal of Genetics*, vol. XVI. (1926), London: Wm. Dawson & Sons Ltd., pp. 287-340 (reprinted 1963).

Amagai et al., "Absorption of Pathogenic Autoantibodies by the Extracellular Domain of Pemphigus Vulgaris Antigen (Dsg3) Produced by Baculovirus," *J. Clin. Invest.*, 94:59-67 (1994).

Amagai et al., "Autoantibodies Against the Amino-Terminal Cadherin-Like Binding Domain of Pemphigus Vulgaris Antigen are Pathogenic," *J. Clin. Invest.*, 90:919-926 (1992).

* cited by examiner

AUTOIMMUNE DISEASE MODEL ANIMAL

The present application claims the benefit of PCT International Application No. PCT/JP00/02023, filed Mar. 30, 2000, which claims benefit of Japanese Patent Application No. 11/91408, filed Mar. 31, 1999, which are hereby incorporated in their entirety.

TECHNICAL FIELD

The present invention relates to autoimmune disease model animals and methods for producing them.

BACKGROUND ART

Pemphigus vulgaris (PV) is an autoimmune disease with involvement of skin and mucous membrane blistering, which is sometimes fatal, and is histologically characterized by blistering in the epidermis as well as immunopathologically characterized by the presence of autoantibody IgG to the cell surface of keratinocyte (Stanley, J. R. Pemphigus. In Dermatology in General Medicine. I. M. Freedberg, A. Z. Eisen, K. Wolff, K. F. Austen, L. A. Goldsmith, S. I. Katz, and T. B. Fitzpatrick, eds. McGraw-Hill, New York, 654–666 (1998)). Patients with pemphigus vulgaris clinically manifest diffuse flaccid blister and erosion. These can be formed in all the stratified squamous epithelia. Without appropriate therapy, the widespread lesions on the skin result in the leakage of body fluid or secondary bacterial infection, and as a result pemphigus vulgaris may be fatal. The prognosis of pemphigus can be improved by systemic administration of corticosteroid and immunosuppression therapy, but the mortality remains considerably high because of death due to complications caused by the therapy.

The target antigen for pemphigus vulgaris was first identified as a 130 kD glycoprotein through immunoprecipitation of keratinocyte extract (Stanley, J. R. et al., J. Clin. Invest. 70:281–288 (1982); Stanley, J. R. et al., J. Clin. Invest. 74:313–320 (1984)). Then, cDNA for the pemphigus vulgaris antigen was isolated via immuno-screening of a human keratinocyte expression library using affinity-purified autoantibody specific to the pemphigus vulgaris antigen (Amagai, M. et al., Cell 67:869–877 (1991)). Nucleotide sequence analysis has revealed that the pemphigus vulgaris antigen belongs to the superfamily of genes for cadherins that are intercellular adhesion molecules. The pemphigus vulgaris antigen is a membrane protein located in desmosome (Karpati, S. et al., J. Cell Biol. 122:409–415 (1993)), and it was named desmoglein 3 (Dsg3) (Amagai, M. Adv. Dermatol. 11:319–352 (1996)).

There is much evidence showing that autoantibody IgG against Dsg3 protein plays a pathogenic role in pemphigus vulgaris. Firstly, it has been reported that activity of the disease correlates to the antibody titer in blood over time by indirect fluorescent antibody technique (Sams Jr, W. M. & Jordon, R. E., Br. J. Dermatol. 84:7–13 (1971)) or ELISA (Ishii, K., et al., J. Immunol. 159:2010–2017 (1997); Amagai, M., et al., Br. J. Dermatol. 140:351–357 (1999)). Secondly, a newborn from the mother affected with pemphigus vulgaris is also transiently affected with the disease due to the IgG transferred across the placenta from the mother (Merlob, P. et al., Pediatrics 78:1102–1105 (1986)). As the IgG derived from the mother is catabolized, the symptom is remitted. Thirdly, the IgG derived from patients with pemphigus vulgaris can induce blistering in tissue-cultured skin in the absence of complement and inflammatory cell (Schiltz, J. R., & Michel, B., J. Invest. Dermatol. 67:254–260 (1976); Hashimoto, K. et al., J. Exp. Med. 157:259–272 (1983)). Fourthly, passive transfer of the IgG derived from sera of patients into newborn mice causes intraepidermal blister formation with typical histological characteristics (Anhalt, G. J. et al., N. Engl. J. Med. 306:1189–1196 (1982)). Fifthly, depletion of patient-derived serum by immuno-absorption using recombinant Dsg3 protein (rDsg3) comprising extracellular domain thereof removes pathogenicity of the serum and inhibits blistering in newborn mice (Amagai, M. et al., J. Clin. Invest. 94:59–67 (1994)). Finally, antibody affinity-purified with rDsg3 exhibits pathogenicity and thus results in the formation of blister with histological characteristics of pemphigus vulgaris in newborn mice (Amagai, M. et al., J. Clin. Invest. 90:919–926 (1992); Amagai, M. et al., J. Clin. Invest. 102:775–782 (1998)).

Based on these studies, pemphigus vulgaris is one of the best-characterized autoimmune diseases with respect to the processes after the generation of autoantibody in particular. Thus pemphigus vulgaris is now an excellent disease model for tissue-specific autoimmune diseases to study cellular mechanisms underlying the production of autoantibody or destruction of self-tolerance, as well as to develop therapeutic methods specific to the diseases. As the first step toward the goals, it is demanded to develop active disease animal model for pemphigus vulgaris.

Most of experimental autoimmune disease animal models are provided by repeated injection of autoantigen with a variety of adjuvants. However, as exemplified by the case of myasthenia gravis, in which the frequency of generation of the active disease in mice immunized with acetylcholine receptor (T. californica) varies considerably depending on the strains, the success of this method is thus highly empirical (Berman, P. W. et al., Ann. N.Y. Acad. Sci. 377:237–57 (1981)).

Previously, an in vivo experimental model for pemphigus vulgaris was developed by the reconstruction of severe combined immunodeficiency (SCID) in mice using PBMC derived from patients with pemphigus vulgaris (Juhasz, I. et al., J. Clin. Invest. 92:2401–7 (1993)). With this model, lymphocytes from the patients produced circulating autoantibody at a low titer, but it was rare that active intraepidermal blistering with deposition of human IgG was found in mouse skin. When human skin was transplanted on SCID mouse, blisters similar to those in pemphigus vulgaris were recognized on the transplanted skin. However, it cannot be denied that the cause of blister formation in this model is an inflammatory response due to the tissue incompatibility with human PBMC and skin. Thus there was no established active disease model for pemphigus vulgaris.

DISCLOSURE OF THE INVENTION

The present invention provides autoimmune disease model animals and a method for producing them. More specifically, the present invention provides non-human mammals showing phenotypes of the autoimmune disease in which activation of T cells and B cells reactive to the antigen protein for the autoimmune disease followed by stable production of autoantibody are induced and provides a method for producing them. In a preferable embodiment, the model animal can be provided by the transplantation of immune cells including B cells producing antibody against the antigen protein of the autoimmune disease and/or T cells that are reactive to the antigen protein.

To achieve the above described objective, first, the present inventors aimed at the production of autoantibody in mice by employing the previously used typical method with repeated injection. Specifically, three strains of mice, BALB/c(H-$2^d$), C3H/HeJ(H-$2^k$), and C57BL/6N(H-$2^b$) were immunized with human or mouse Dsg3 protein. Complete Freund's adjuvant was used in the primary immunization, and then booster immunization was carried out 3 or 7 times by using incomplete Freund's adjuvant. However, with this method, no mice produced antibody capable of reacting to mouse Dsg3 protein (Table 1) and showed phenotype of *pemphigus vulgaris* at all.

Based on this result, the present inventors set up the hypothesis that self-tolerance to Dsg3 protein prevents the production of pathogenic antibody in mouse body. According to the hypothesis, it can be assumed that the immune system is not exposed to Dsg3 protein during the developmental stages in Dsg3-deficient mouse created by gene-targeting technique and thus the mouse does not acquire self-tolerance to Dsg3 protein.

In order to demonstrate the hypothesis, the present inventors studied whether it was possible for Dsg3-deficient mouse immunized with Dsg3 protein to produce antibody against Dsg3 protein. From the result, it was revealed that when immunized with Dsg3 protein a homozygous DSG3 gene-deficient DSG3−/− mouse much more efficiently produced the antibody than a heterozygous DSG3 gene-deficient DSG3+/− mouse (FIG. 1A). In addition, the antibody produced by DSG3−/− mouse was capable of binding to mouse Dsg3 protein on the keratinocyte, but the antibody from DSG3+/− mouse was not (FIG. 1B). Specifically, it was revealed that self-tolerance to DSG3 protein had not been established in DSG3−/− mouse and the produced antibody recognized mouse Dsg3 protein as an antigen.

Thus, the present inventors next aimed at the production of antibody against Dsg3 protein and expression of phenotype of *pemphigus vulgaris* in RAG2−/− immunodeficiency mouse by collecting splenocytes (which have capability of producing antibody against DSG3 protein) from DSG3−/− mouse immunized with Dsg3 protein and adoptively transferring them into the immunodeficiency mouse. Such RAG2−/− mice express Dsg3 protein, but the mice have neither mature T cells nor B cells because they are deficient in rearrangement of T cell receptor genes and immunoglobulin genes (namely, they are immunodeficient).

As a result, in RAG2−/− mice in which splenocytes from DSG3−/− mouse had been transplanted, the encounter of Dsg3 protein-specific lymphocytes among splenocytes with endogenous Dsg3 protein resulted in permanent production of the antibody against Dsg3 protein (FIG. 2A). In addition, it was found that RAG2−/− mice having the immunized DSG3−/− splenocytes showed nearly identical phenotype of DSG3−/− mouse (Koch, P. J., et al., J. Cell Sci. 111: 2529–2537 (1998); Koch, P. J., et al., J. Cell Biol. 137: 1091–1102 (1997)). All of the mice exhibited erosive lesions in mucous membranes with epidermal separation just above the basal cell layer and telogen hair loss (FIG. 3). The presence of nearly identical phenotype reproduced by adoptive transfer of DSG3−/− splenocytes in RAG2−/− recipient mice demonstrated that the produced antibody was specific and pathogenic.

The specificity of the antibody can also be verified by the fact that the in vivo deposition is not detectable in other simple epithelia expressing Dsg2 protein (Schafer, S. et al., Exp. Cell Res. 211:391–9 (1994)) and upper part of epidermis expressing Dsg1 protein (FIG. 3G) (Amagai, M. et al., J. Invest. Dermatol. 106:351–355 (1996)).

Thus, the present invention provides the first disease mouse model for *pemphigus* and a method for producing them. The method of the present invention, because of the nature thereof, can be widely applicable to the preparation of model animals for other autoimmune diseases in which associated autoimmune targets have been identified.

Accordingly the present invention relates to autoimmune disease model animals and a method for producing them, more specifically relates to:

(1) a non-human mammal showing a phenotype of autoimmune disease through production of an antibody reacting to an antigen protein for an autoimmune disease or T cell activation;

(2) the non-human mammal of (1), wherein immune cells from a non-human mammal lacking an antigen gene for the autoimmune disease have been transplanted to the non-human mammal;

(3) the non-human mammal of (1), wherein immune cells from a non-human mammal that lacks the antigen gene for the autoimmune disease and that has been immunized with the antigen protein have been transplanted to the non-human mammal;

(4) the non-human mammal of (2) or (3), wherein the immune cells are transplanted to an immunodeficient non-human mammal;

(5) the non-human mammal of (4), wherein the immunodeficient non-human mammal is a non-human mammal that lacks the RAG2 gene;

(6) the non-human mammal of any one of (2) to (5), wherein the immune cells are splenocytes;

(7) the non-human mammal of any one of (1) to (6), wherein the autoimmune disease is *pemphigus vulgaris*;

(8) the non-human mammal of (7), wherein the antigen protein is desmoglein 3 protein;

(9) the non-human mammal of any one of (1) to (8), wherein the non-human mammal is a rodent;

(10) the non-human mammal of (9), wherein the rodent is a mouse;

(11) a method for producing a non-human mammal showing a phenotype of autoimmune disease through production of an antibody reacting to an antigen protein for an autoimmune disease or T cell activation, which comprises the steps of:

(a) immunizing, with the antigen protein for the autoimmune disease, a non-human mammal that lacks the antigen gene for the autoimmune disease, (b) preparing immune cells from the non-human mammal, and (c) transplanting the immune cells to a non-human mammal having the antigen protein;

(12) the method of (11), wherein the immune cells are transplanted to an immunodeficient non-human mammal;

(13) the method of (12), wherein the immunodeficient non-human mammal is a non-human mammal that lacks the RAG2 gene;

(14) the method of any one of (11) to (13), wherein the immune cells are splenocytes;

(15) the method of any one of (11) to (14), wherein the autoimmune disease is *pemphigus vulgaris*;

(16) the method of (15), wherein the antigen protein is desmoglein 3 protein;

(17) the method of any one of (11) to (16), wherein the non-human mammal is a rodent; and

(18) the method of (17), wherein the rodent is a mouse.

The model animal of the present invention can show phenotype of autoimmune disease through the stable production of antibody reacting to the antigen protein for the autoimmune disease or sustained activation of T cell.

There is no particular restriction on the type of objective disease for which model animals are to be prepared in accordance with the present invention, as far as the disease is an autoimmune disease. Such autoimmune diseases include, for example, but not limited to, *pemphigus vulgaris*, myasthenia gravis, autoimmune hemolytic anemia, Basedow's disease, Hashimoto's disease, Goodpasture's syndrome, autoimmune diabetes mellitus, multiple sclerosis, etc.

Animals to be utilized for creating the model animal are preferably non-human mammals. There is no restriction on such non-human mammals, as far as gene-disrupted animals can be created from them. Preferable animals include rodents, e.g., mouse.

The model animals in accordance with the present invention can be created by immunizing antigen gene-deficient non-human mammals with the antigen protein for the autoimmune disease, removing the immune cells thereof, and then transplanting the cells to other non-human mammals having the antigen protein.

Animals having the disputed antigen gene can be created by a method known to those skilled in the art. The antigen gene to be disrupted includes, for example, but not limited to, the DSG3 gene when the autoimmune disease is *pemphigus vulgaris*; the acetylcholine receptor gene for myasthenia gravis; the TSH receptor gene for Basedow's disease or Hashimoto's disease; the type IV collagen gene for Goodpasture's syndrome; the myelin basic protein gene for multiple sclerosis, etc.

Further, immune cells can be obtained from the thymus, lymph node, spleen, liver, intestinal epithelium, peripheral blood, etc. but are not limited to those from the tissues. The spleen abundantly contains mature immune cells and thus is a preferable organ for the immune cells. It is preferable that the animal (donor) from which immune cells are prepared and the animal (recipient) to which lymphocytes derived from the immune cells are transferred belong to a same species and have a same genetic background thereby preventing the onset of GVHD which may cause tissue destruction in the recipient.

In addition to this, it is preferable that the recipient has immunodeficiency thereby preventing the rejection of lymphocytes derived from immune cells transferred. For example, SCID mouse, nude mouse as well as an animal of which RAG2 gene has been disrupted may be used as the immunodeficient animal. Furthermore, MHC-knockout mouse or common γ chain-knockout mouse can also be used but it is not limited thereto.

The immunization with the antigen protein from the donor, preparation of immune cells from the donor, and transplantation of the immune cells to the recipient can be carried out, for example, by the methods as described in the Examples.

The model animal created in accordance with the present invention can show phenotype of autoimmune disease through the stable production of antibody reacting to the antigen protein for the autoimmune disease or sustained activation of T cell. In the model animal for *pemphigus vulgaris*, major phenotype includes weight loss and reversible telogen hair loss. Further, among autoimmune diseases other than *pemphigus vulgaris*, phenotype may include reduced muscle power in myasthenia gravis; anemia in autoimmune hemolytic anemia; hyperthyroidism in Basedow's disease; hypothyroidism in Hashimoto's disease; nephropathy and pulmonary disorders in Goodpasture's syndrome; glucosuria in autoimmune diabetes mellitus; and neuroparalysis in multiple sclerosis.

One can use these model animals for developing therapeutic agents or methods for the diseases, administering to them test compounds of interest for therapeutic effects on autoimmune diseases and observing phenotypes thereof. Particularly the major phenotype includes weight loss and reversible telogen hair loss in *pemphigus vulgaris* model mouse prepared in accordance with the present Example and the phenotypes last over 6 months, and therefore it is possible to readily and objectively evaluate the effectiveness of each therapeutic agent or method based on the observation without sacrificing the mouse. In addition, these model mice are very useful for clarifying cellular mechanism underlying the production of antibody against the antigen protein.

BEST MODE FOR CARRYING OUT THE INVENTION

Figure 1:
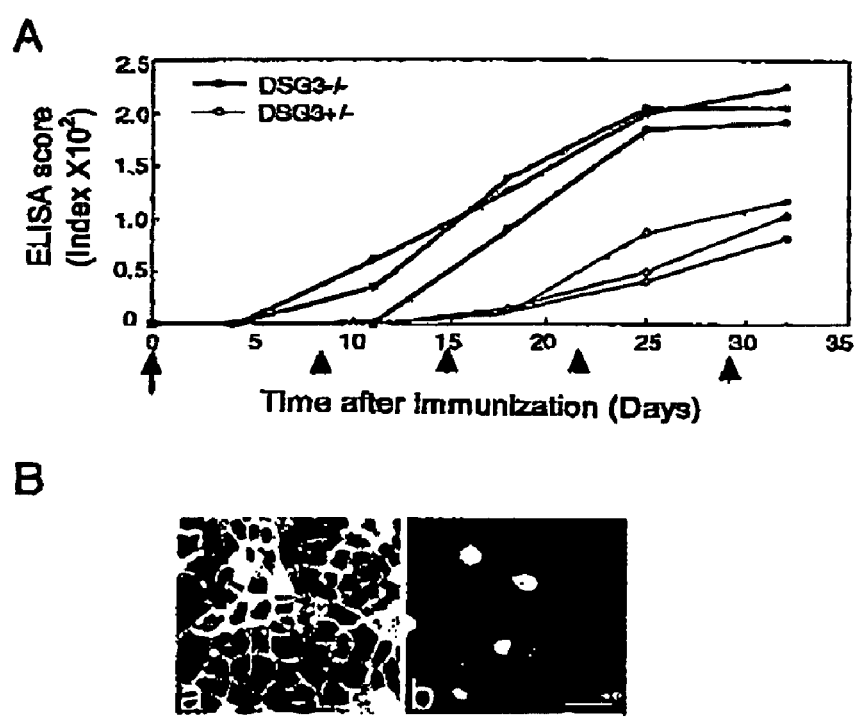
FIG. 1 shows a diagram (A) and photograph (B) displaying the production of anti-Dsg3 IgG that is capable of in vivo binding in DSG3−/− mouse. (A): DSG3−/− mouse and the +/− littermate mice thereof were immunized with mouse rDsg3, and then the titers of anti-Dsg3 IgG were measured over time by ELISA. An arrow indicates the primary immunization with mouse rDsg3 using complete Freund's adjuvant, and an arrow head indicates booster immunization with mouse rDsg3 using incomplete Freund's adjuvant. DSG3−/− mouse efficiently produced much more anti-Dsg3 IgG than the +/− littermate mice. (B): while intercellular junctions of cultured keratinocytes were stained with the serum derived from the immunized DSG3−/− mouse (a), they were not stained with the serum derived from the +/− littermate mice (b) Bar represents 50 µm.

The present invention is illustrated in detail below with reference to Examples, but is not to be construed as being limited thereto.

EXAMPLE 1

Production of Recombinant Mouse Dsg3 Protein

A cDNA encoding the entire extracellular domain of mouse Dsg3 (Genbank U86016) was amplified by PCR using appropriate primers (5'-CCGAGATCTC-CTATAAATATGACCTGCCTCTTCCCTAGA-3'/SEQ ID NO: 1, 5'-CGGGTCGACCCTCCAGGATGACTC-CCCATA-3'/SEQ ID NO: 2) and using a phage clone containing mouse Dsg3 cDNA (a gift from Dr. Jouni Uitto) as a template; amplified fragment was subcloned (pEVmod-mDsg3-His) by replacing it with human Dsg3 cDNA in pEVmod-Dsg3-His vector (Ishii, K., et al., J. Immunol. 159:2010–2017 (1997)). A recombinant baculo-protein, mouse rDsg3, was prepared as described previously (Amagai, M. et al., J. Clin. Invest. 94:59–67 (1994); Amagai, M. et al., J. Invest. Dermatol. 104:895–901 (1995)).

EXAMPLE 2

Immunization of Wild-Type DSG3+/+ Mouse with Mouse Dsg3 Protein

First, attempts were made to produce antibodies against Dsg3 protein in a variety of wild-type mouse strains after immunizing with human or mouse rDsg3 (Table 1).

Mice were sensitized with 5 μg of purified mouse or human rDsg3 by intraperitoneal injection with complete Freund's adjuvant (CFA). Then booster immunization was carried out every week, 3 or 7 times, with mouse or human rDsg3 using incomplete Freund's adjuvant (IFA). An ELISA test for antibody production was conducted 3 days after each booster immunization.

In ELISA assay for blood IgG against mouse Dsg3 protein (mDsg3) or human Dsg3 protein (hDsg3) in mice, mouse or human rDsg3 was used as a coating antigen. More specifically, a 96-well microtiter plate was coated with 100 μl of 5 μg/ml purified mouse or human rDsg3 at 4° C. overnight. All serum samples were diluted 50 to 5,000 times and then incubated on a 96-well ELISA plate at room temperature for 1 hour. After the samples were incubated with peroxidase-conjugated goat anti-mouse IgG antibody (MBL, Nagoya, Japan) at room temperature for 1 hour, the coloring reaction was carried out by using 1 mM tetramethylbenzidine as a substrate for peroxidase (Ishii K et al. J Immunol 159:2010–2017, 1997; Amagai M et al., Br J Dermatol 140:351–357, 1999). The respective samples were analyzed in duplicate. A single serum sample obtained from DSG3−/− mouse immunized with mouse rDsg3 was used as a positive control and serum derived from a non-immunized mouse was used as a negative control. ELISA score was obtained as an exponent in a value calculated by [(sample OD−negative control OD)/(positive control OD−negative control OD)×100] (Table 1).

Further, the production of antibody against Dsg3 protein was tested by immuno-fluorescent staining of cultured keratinocytes. Mouse keratinocytes from cell line PAM212 (Yuspa, S. H. et al., Cancer Res. 40:4694–4703 (1980)) or human keratinocytes from cell line KU8 (Tsukamoto, T., Keio J. Med. 38:277–293 (1989)) were incubated together with mouse serum sample 20-fold diluted with DMEM containing 10% FCS at 37° C. under humid air containing 5% $CO_2$ for 30 minutes. Subsequently the cells were washed with PBS(−) and then fixed with 100% methanol at −20° C. for 20 minutes; the cells were incubated with fluorescein isothiocyanate (FITC)-labeled goat anti-mouse IgG antibody (DAKO, Copenhagen, Denmark) at room temperature for 30 minutes. The stain was observed with a fluorescence microscope (Nikon, Eclipse E800).

The ELISA and immuno-fluorescence staining revealed that C57BL/6N mouse or BALB/c mouse produced IgG capable of reacting to only human rDsg3 but not to mouse rDsg3 when immunized with human rDsg3 first using complete Freund's adjuvant and then using incomplete Freund's adjuvant. Merely C3H/HeJ mice produced IgG capable of weakly cross-reacting to mouse rDsg3, when observed by ELISA. When these three strains of mice were immunized with mouse rDsg3, no mice from the three strains produced IgG recognizing mouse or human rDsg3 in the evaluation by three methods (ELISA, indirect fluorescent antibody technique, and living keratinocyte staining). These findings suggested that wild-type DSG3+/+ mouse had immunotolerance to Dsg3 and thus it was difficult to allow for DSG3+/+ wild-type mouse to produce antibody against mouse Dsg3.

TABLE 1

| Mouse strain | n | Antigen[a] | CFA | IFA[b] | ELISA[c] mDsg3 | ELISA[c] hDsg3 | IIF[d] NMS | IIF[d] NHS | Living cell staining[e] Pam | Living cell staining[e] KU8 |
|---|---|---|---|---|---|---|---|---|---|---|
| C57BL/6N | 2 | hDsg3 | 1 | 3 | 18.4 | 93.4 | − | + | − | + |
| BALB/c | 3 | hDsg3 | 1 | 3 | 6.3 | 85.4 | − | + | − | + |

TABLE 1-continued

| Mouse strain | n | Antigen[a] | CFA | IFA[b] | ELISA[c] | | IIF[d] | | Living cell staining[e] | |
|---|---|---|---|---|---|---|---|---|---|---|
| | | | | | mDsg3 | hDsg3 | NMS | NHS | Pam | KU8 |
| C3H/HeJ | 2 | hDsg3 | 1 | 3 | 47.5 | 167.7 | − | + | − | + |
| C57BL/6N | 3 | mDsg3 | 1 | 7 | 10.6 | 10.1 | − | − | − | − |
| BALB/c | 3 | mDsg3 | 1 | 7 | 1.7 | 2.3 | − | − | − | − |
| C3H/HeJ | 3 | mDsg3 | 1 | 7 | 6.4 | 7.5 | − | − | ND | ND |

When recombinant human Dsg3 was used, "hDsg3" is provided in the column of antigen in Table 1; when recombinant mouse Dsg3 was used, "mDsg3" is provided (a). In the column of "CFA," the number of immunization treatments with purified mouse or human recombinant Dsg3 using complete Freund's adjuvant (CPA) is indicated; in the column of "IFA," the number of booster immunizations conduced every week after the first one using incomplete Freund's adjuvant (IFA) (3 or 7 times) is indicated (b) ELISA score was computed for human recombinant Dsg3 (hDsg3) or mouse recombinant Dsg3 (mDsg3) (c); if higher than 20.0, it can be judged as positive. "IIF" of this Table indicates a result of indirect fluorescence antibody staining (IIF) of normal mouse skin (NMS) or normal human skin (NHS) by using mouse serum (d). Further, "living cell staining" of this Table indicates a result of living cell staining for cultured mouse keratinocytes from a cell line (Pam) or human keratinocytes from a cell line (KU8) by using the mouse serum (e). "−" means negative; "+" means positive. "ND" indicates that the test was not done.

EXAMPLE 3

Immunization of DSG3−/− Mouse and DSG3+/− Mouse with Mouse Dsg3 Protein

DSG3−/− mice were prepared by mating male DSG3−/− mice with female DSG3+/− mice (Koch, P. J., et al., J. Cell Biol. 137:1091–102 (1997)). RAG2−/− mice, which had been obtained by back-crossing with B6.SJL-ptpr$^c$ over 10 generations, were provided from Taconic (German Town, N.Y.) (Schulz, R.-J. et al., J. Immunol. 157:4379–4389 (1996)).

ELISA scores for mouse rDsg3 were determined after immunizing DSG3−/− mouse with mouse rDsg3 in order to verify the absence of immuno-tolerance to Dsg3 protein in DSG3−/− mouse.

Both DSG3−/− mice and DSG3+/− mice were sensitized with 5 μg of purified mouse rDsg3 by using complete Freund's adjuvant (0 day), and then booster was carried out with mouse rDsg3 by using incomplete Freund's adjuvant after 8, 15, 22, and 28 days. The antibody production was tested by ELISA using mouse rDsg3 as a coating antigen in the same manner as in Example 2.

The production of anti-Dsg3 IgG was found as early as $11^{th}$ day in DSG3−/− mice (n=4) and the titer continued to increase (FIG. 1A). When DSG3+/− mice were immunized repeatedly, the ELISA titer eventually increased, but the titer was significantly lower than the titer for DSG3−/− mice observed on the $32^{nd}$ day (p<0.0001).

To determine whether the anti-Dsg3 IgGs produced by these mice can bind to Dsg3 protein on the keratinocytes in vivo, the same staining as in Example 2 was carried out by using mouse keratinocytes from a cell line Pam212. When the serum derived from DSG3−/− mouse was added to culture media, the serum bound at intercellular adhesion sites of cultured keratinocytes. However, no stain was detectable on the cell surface by using sera derived from DSG3+/− mouse at all (FIG. 1B). There was no in vivo IgG deposition in the epidermis of the immunized DSG3+/− mice. Thus there is an extremely high possibility that the antibodies produced by DSG3+/− mouse are those against trace quantities of contaminants in purified mouse rDsg3, against the C-terminal tag of mouse rDsg3, or against masked Dsg3 epitopes which are not accessible under the in vivo condition.

These results suggested that there was no immuno-tolerance to Dsg3 in DSG3−/− mouse and thus pathogenic IgG inhibiting Dsg3 function for adhesion was produced via immunizing DSG3−/− mouse with mouse rDsg3.

EXAMPLE 4

Permanent Production of Pathogenic Anti-Dsg3 IgG in Recipient RAG2−/− Mouse

Because DSG3−/− mouse has the deficient target antigen, it was predicted that anti-Dsg3 IgG did not affect the phenotype in DSG3−/− mouse. Thus, an experiment was conducted where immunized splenocytes from DSG3−/− mouse or DSG3+/− mouse were transferred into RAG2−/− immunodeficiency mouse. RAG2−/− mouse expresses Dsg3 protein but has neither mature T cells nor B cells because neither T cell receptor genes nor immunoglobulin genes can be rearranged in the mouse. Therefore it is assumed that the transferred splenocytes are not rejected and anti-Dsg3 IgG can be produced in the recipient mouse.

DSG3−/− mice and DSG3+/− mice were sensitized with 5 μg of purified mouse rDsg3 by using complete Freund's adjuvant (0 day). Then booster immunization was carried out with mouse rDsg3 using incomplete Freund's adjuvant after 7 and 14 days. The production of antibody was confirmed on the $18^{th}$ day by ELISA in the same manner as in Example 2. Finally, booster immunization was carried out with mouse rDsg3 but without any adjuvant, and the mice were sacrificed several days after the booster immunization to prepare splenocytes as immune cells.

To perform the adoptive transfer of splenocytes, monocytes were isolated from the spleens of DSG3−/− mice or DSG3+/− mice and re-suspended in complete RPMI1640 medium (Nissui Pharmaceuticals, Tokyo) containing 10% fetal bovine serum, 0.21% sodium bicarbonate solution (w/v), 2 mM L-glutamine (GIBCO), and antibiotics. About $1×10^7$ splenocytes were suspended in PBS and transferred into RAG2−/− mouse via caudal vein by intravenous injection. The production of antibody was tested by ELISA using mouse rDsg3 as a coating antigen in the same manner as in Example 2.

Figure 2:
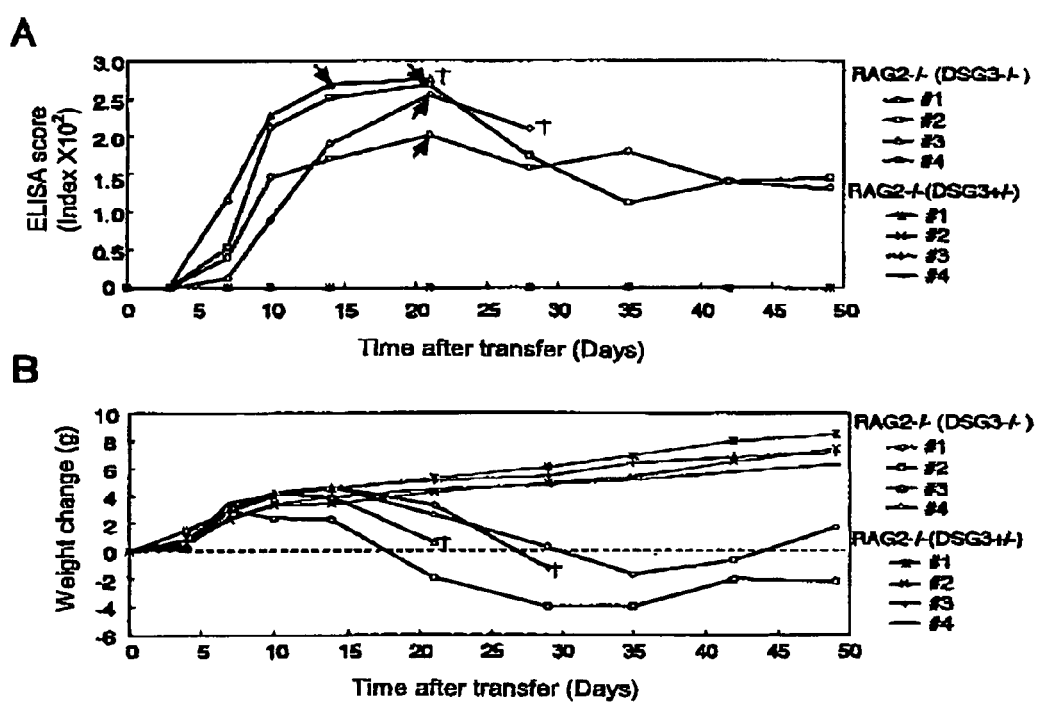
FIG. 2 shows the production of anti-Dsg3 IgG in recipient RAG2−/− mice after the transfer of the immunized DSG3−/− splenocytes. (A): ELISA scores to mouse rDsg3 were obtained with RAG2−/− mouse that had received splenocytes from the immunized DSG3−/− mouse [RAG2−/− (DSG3−/−)] or RAG2−/− mouse that had received splenocytes from the immunized DSG3+/− mouse [RAG2−/− (DSG3+/−)]. The RAG2−/− mouse having DSG3−/− splenocytes had the sustained production of anti-Dsg3 IgG. An arrow indicates the first day of telogen hair loss phenotype. In contrast, ELISA for RAG2−/− mouse having DSG3+/− splenocytes was always negative over time. (B): the time course of varying body weight of recipient RAG2−/− mouse was plotted. After 10 to 14 days, the increase in weight delayed in RAG2−/− mice having DSG3−/− splenocytes as compared with mice having DSG3+/− splenocytes, and then the weight continued to decrease. Several mice died (†), but the remaining several mice survived and then their weights increased.

Anti-Dsg3 IgG was detected in the blood of recipient RAG2−/− mice as early as $4^{th}$ day after the transfer of DSG3−/− splenocytes. The antibody produced rapidly increased and reached a plateau around the 21$^{st}$ day; the production then continued permanently (n=13) (FIG. 2A). The sustained antibody production was observed for 6 months or more until the mice died. In contrast, anti-Dsg3 IgG was always undetectable over time in the blood of RAG2−/− mice in which DSG3+/− mouse splenocytes had been transferred (n=5) (FIG. 2A).

In order to determine the localization of B cells producing anti-Dsg3 IgG, ELISPOT assay was conducted as follows. A 96-well microtiter plate of which bottom is made of PVDF (Millipore-Amicon, Beverly, Mass.) was coated with mouse rDsg3 of 30 µg/ml. The monocytes prepared form reconstructed RAG2−/− mouse peripheral blood, spleen, bone marrow, and lymph node were incubated on the plate at 37° C. under humid air containing 5% $CO_2$ for 4 hours. The IgG bound to the membrane was visualized as a spot by using alkaline phosphatase-conjugated anti-mouse IgG antibody (Zymed Laboratories Inc, San Francisco, Calif.). The number of spots were counted under a stereoscopic microscope, the frequency of B cells producing anti-mDsg3 IgG was determined as the number per $10^5$ monocytes. All the experiments were performed in triplicate. The number of B cells producing anti-Dsg3 IgG determined by the assay is shown in Table 2.

Figure 3:
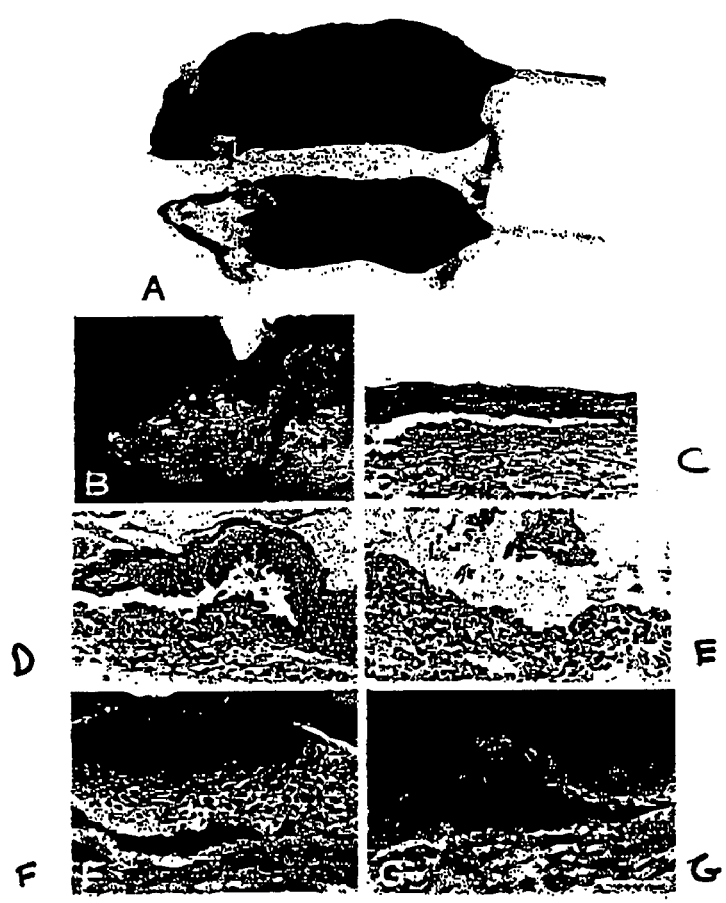
FIG. 3 is a photograph showing the expression of *pemphigus vulgaris* phenotype in RAG2−/− mice in which the immunized DSG3−/− splenocytes have been transferred. Around 7 to 14 days after the transfer of splenocytes, weight loss was recognized in RAG2−/− mice having DSG3−/− splenocytes (A, bottom) when compared with mice having DSG3+/− splenocytes (A, top). Several mice showed the onset of erosion with scab around noses and cheeks where they scratched (B). Based on histological diagnosis of RAG2−/− mouse having DSG3−/− splenocytes, intraepidermal blister formation was found immediately above the basal layer of mucosal epithelium (C, hard palate; D, upper part of the esophagus). Inflammatory infiltrates were recognized below the erosion foci (E, upper part of the esophagus). In vivo IgG deposition was recognized on cellular surface of keratinocyte in mucosal epithelium by direct immunofluorescence method (F, hard palate) and skin (G, around nose) (white part of the diagram). Bar represents 50 µm.

It was revealed that B cells producing anti-Dsg3 IgG were localized in the spleens and lymph nodes of recipient RAG2−/− mice in the early phase (on the 22$^{nd}$ day) as well as late phase (on the 117$^{th}$ day) after the adoptive transfer (Table 2). In this Table, RAG2−/− mice in which splenocytes from immunized DSG3−/− mouse had been transferred is represented by "+"; the mouse which had no transferred cell is by "−" (a) "Days" represents days from the transfer to the sacrifice (b). The number of B cells producing anti-mDsg3 IgG is indicated as the number per $10^5$ monocytes (c). The frequency of B cells producing anti-Dsg3 IgG in the spleen ranged from 20 to 100 cells per $10^5$ monocytes.

oral cavity (FIG. 3F, hard palate), and esophagus mucous membrane in recipient RAG2−/− mouse. In epidermis consisting of several layers of keratinocytes, the presence of IgG deposition was restricted to the lower layers (FIG. 3G), while IgG was observed in all the epithelial layers in epithelia of oral cavity and esophagus (FIG. 3F). IgG deposition was not detected in any other tissues including heart, lung, liver, kidney, stomach, small intestine, and large intestine in these mice. Histological diagnosis of RAG2−/− mice having immunized DSG3−/− splenocytes showed the presence of intraepithelial cleavage immediately above the basal layer, namely, acantholysis immediately above the basal layer which is a typical characteristic of *pemphigus vulgaris*, in buccal mucous membrane, hard palate (FIG. 3C), the oral and pharyngeal region, and upper part of the esophagus (FIG. 3D). The significant inflammatory cell infiltrate was not essentially seen in blistering lesions in the early phase (FIG. 3C). Inflammatory infiltrate was chiefly found in old erosion foci (FIG. 3E). Irritation and acute inflammation secondarily caused by food were recognized there, which were due to loss of epithelial barrier function. It can be presumed that these damages perhaps reduced ingestion in the mice and resulted in growth inhibition.

In contrast, no phenotypic or pathological alterations were recognized in RAG2−/− mice having immunized DSG3+/− splenocytes. These findings suggested that RAG2−/− mice having immunized DSG3−/− splenocytes expressed *pemphigus vulgaris* phenotype.

EXAMPLE 6

RAG2−/− Mouse Having Immunized DSG3−/− Splenocytes Exhibited the Phenotype of Telogen Hair Loss About 15 to 25 days after the adoptive transfer, partial hair loss was recognized in 11 of 13 RAG2−/− mice (FIG. 2A,

TABLE 2

| Mouse | Transfer$^a$ | Days$^b$ | Spleen | Lymph node | Bone marrow | PBMC |
|---|---|---|---|---|---|---|
| RAG #466 | − | − | 0.0 ± 0.0$^c$ | 0.0 ± 0.0 | 0.0 ± 0.0 | 0.0 ± 0.0 |
| RAG #514 | + | 22 | 86.5 ± 29.9 | 13.5 ± 13.6 | 0.0 ± 0.0 | 3.8 ± 5.4 |
| RAG #212 | + | 33 | 102.1 ± 14.7 | 47.8 ± 8.8 | 0.0 ± 0.0 | 0.0 ± 0.0 |
| RAG #134 | + | 117 | 20.8 ± 5.9 | 16.5 ± 5.9 | 2.1 ± 2.9 | 0.0 ± 0.0 |
| RAG #135 | + | 117 | 31.3 ± 8.8 | 27.1 ± 2.9 | 0.0 ± 0.0 | 0.0 ± 0.0 |

EXAMPLE 5

RAG2−/− Mouse Having Immunized DSG3−/− Splenocytes Expressed the Phenotype of *Pemphigus vulgaris*

The first recognized symptom in recipient RAG2−/− mouse having immunized DSG3−/− splenocytes was weight loss (n=13) as compared with mouse having DSG3+/− splenocytes (n=5) around 7 to 14 days after the adoptive transfer (FIGS. 2B and 3A). The weights of these mice then continued to decrease and several of them actually died. The remaining survived mice later began to gain their weights (FIG. 2B). The phenotype of weight loss was recognized in all the recipient RAG2−/− mice examined (n=13). Several of the recipient RAG2−/− mice (n=5) had the onset of erosion with scab on the skin around the noses which is a common area of scratch (FIG. 3B).

Figure 4:
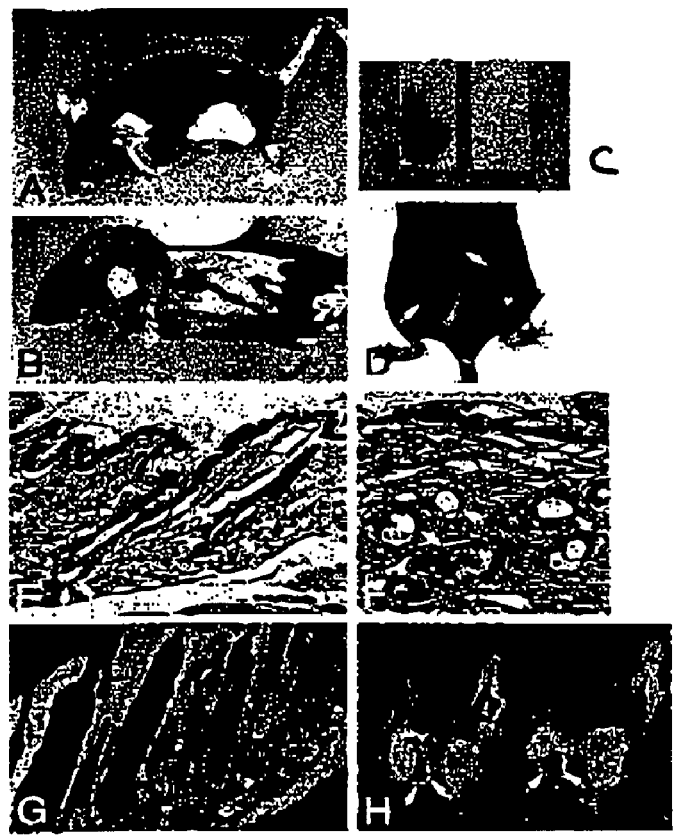
FIG. 4 is a photograph showing a telogen hair loss phenotype of RAG2−/− mouse, in which the immunized DSG3−/− splenocytes had been transferred, similar to that observed in DSG3−/− mouse. About 15 to 25 days after the transfer, RAG2−/− mouse having DSG3−/− splenocytes showed partial hair loss (A, B). In hair-pull test with adhesive tape, a bunch of hairs were adhered on the tape in the case of RAG2−/− mouse having DSG3−/− splenocytes (C, left), but no hair was adhered in the case of RAG2−/− mouse having DSG3+/− splenocytes (C, right). After that, a mosaic of new hair was recovered in the area without hair (D, arrow). Histological diagnosis showed the presence of acantholysis between cells of hair bulb and basal layer of outer root sheath epithelium (E, arrow) as well as the presence of empty expanded telogen hair follicle (F, arrow). By direct immunofluorescence method, in vivo IgG deposition was found on the cellular surface of keratinocyte in the hair root (G, H) (white part of the diagram). Bar represents 50 μm.

In vivo IgG deposition was found on the cell surface of stratified squamous epithelium keratinocyte including epidermis (FIG. 3G; around the nose), mucous membrane of see arrow, FIG. 4A, B). Typically, hair loss was initiated as a small spot, and then was expanding gradually during the next 2 to 3 weeks. Hair loss was initiated in the forehead in recipient RAG2−/− mice of 12-week old or less, and it further expanded backward. A mosaic of new hair was recovered in the telogen hair loss spot in several mice, but there were mice in which telogen hair loss spots remained without changing for one month or more or in which telogen hair loss expanded without forming demarcated telogen hair loss spot (FIG. 4D). When adhesive tape was adhered to the area adjacent to a telogen hair loss spot and then removed (hair-pull test) (Koch, P. J., et al., J. Cell Sci. 111:2529–2537 (1998)), a bunch of hairs adhered on the tape (FIG. 4C). These phenotypes lasted for 6 months or more as far as anti-Dsg3 IgG was present in the blood.

The skin biopsy of RAG2−/− recipient mouse revealed intense IgG deposition on the cell surface of keratinocytes around hair bulb (FIGS. 4G, H). The intensity of IgG binding in hair follicle was much higher than that in epi dermis (FIG. 4G). Histological diagnosis of the skin showed the presence of acantholysis between cells around hair bulb at the resting stage and the basal layer of outer root sheath (FIGS. 4E, H; arrow). In telogen hair loss spots, there were empty expanded telogen hair follicles being consistent with telogen effluvium (FIG. 4F). There was no evident acantholysis in the surface layer of epidermis without damage. No obvious infiltration of inflammatory cells was recognized around the hair follicles with acantholysis (FIGS. 4E, F).

In contrast, no telogen hair loss spots were always found in RAG2−/− mice in which DSG3+/− splenocytes had been transferred.

INDUSTRIAL APPLICABILITY

The development of this model provided a new direction for the study of tissue-specific autoimmune diseases (autoimmune diseases in which the relation between target antigen and toxic antibody or T cell has been clarified). The model of the present invention is useful to elucidate cellular mechanisms underlying the production of antibody against antigen protein for an autoimmune disease and induction of cytotoxic T cell by particularly modifying lymphocytes before adoptive transfer. This model can also be a valuable tool for the development of new disease-specific therapies. Because, in the *pemphigus vulgaris* model animal in accordance with the present invention, the major phenotypes are weight loss and reversible telogen hair loss, activity of the disease can be monitored by observing the mice without sacrificing them. ELISA titer of blood anti-Dsg3 antibody is also an objective index for the disease activity. Further, the phenotype remains expressed for 6 months or more. Thus efficacy of each therapeutic method can readily and objectively be evaluated. More importantly, the method of the present invention is applicable for the development of active disease mouse models for other tissues specific autoimmune diseases in which target antigens have been identified.

The invention claimed is:

1. A method for producing a mouse recipient that produces an antibody reactive to an antigen protein for an autoimmune disease and/or has activated T cells reactive to the antigen protein, which comprises the steps of:
    (a) immunizing, with the antigen protein for the autoimmune disease, a mouse donor that (i) lacks a gene encoding the antigen protein and (ii) develops immune cells,
    (b) preparing immune cells from the donor, and
    (c) transplanting the immune cells to the recipient that (iii) is the same species as the donor, and (iv) has the same genetic background and/or is immunodeficient, thereby producing a mouse recipient that produces an antibody reactive to an antigen protein for an autoimmune disease and/or has activated T cells reactive to the antigen protein, wherein the antigen protein is desmoglein 3 protein and the autoimmune disease is *pemphigus vulgaris*.

2. The method of claim 1, wherein the recipient is immunodeficient.

3. The method of claim 2, wherein the recipient lacks a RAG2 gene.

4. The method of claim 1, wherein the immune cells are splenocytes.

* * * * *

SEQUENCE LISTING

```
<160> NUMBER OF SEQ ID NOS: 2

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:  primer

<400> SEQUENCE: 1
ccgagatctc ctataaatat gacctgcctc ttccctaga                              39

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:  primer

<400> SEQUENCE: 2
cgggtcgacc ctccaggatg actccccata                                        30
```